United States Patent
De Keyser et al.

(10) Patent No.: US 10,323,025 B2
(45) Date of Patent: Jun. 18, 2019

(54) CRYSTALLIZATION PROCEDURE FOR OBTAINING CANAGLIFLOZIN HEMIHYDRATE CRYSTALS

(71) Applicant: Janssen Pharmaceutica NV, Beerse (BE)

(72) Inventors: Ruben De Keyser, Beerse (BE); Stijn Laps, Beerse (BE); Thomas Joachim Landewald Rammeloo, Beerse (BE); Koen Johan Herman Weerts, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/064,084

(22) PCT Filed: Dec. 20, 2016

(86) PCT No.: PCT/EP2016/081861
§ 371 (c)(1),
(2) Date: Jun. 20, 2018

(87) PCT Pub. No.: WO2017/108752
PCT Pub. Date: Jun. 29, 2017

(65) Prior Publication Data
US 2019/0002449 A1   Jan. 3, 2019

(30) Foreign Application Priority Data

Dec. 21, 2015  (EP) .................................... 15201459
May 31, 2016  (EP) .................................... 16172070

(51) Int. Cl.
*C07D 409/00*  (2006.01)
*C07D 409/10*  (2006.01)

(52) U.S. Cl.
CPC ........ *C07D 409/10* (2013.01); *C07B 2200/13* (2013.01)

(58) Field of Classification Search
CPC .......................... C07D 409/10; C07B 2200/13
USPC .......................................................... 549/60
See application file for complete search history.

(56) References Cited

U.S. PATENT DOCUMENTS

2012/0108824 A1* 5/2012 Rammeloo .......... C07D 309/10
549/60

FOREIGN PATENT DOCUMENTS

| WO | WO 2005/012326 A1 | 2/2005 |
| WO | WO 2008/069327 A1 | 6/2008 |
| WO | WO 2011/003976 A1 | 1/2011 |
| WO | WO 2014/180872 A1 | 11/2014 |

OTHER PUBLICATIONS

International Search Report and Written Opinion issued in related application No. PCT/EP2016/081861, dated Apr. 3, 2017.

* cited by examiner

*Primary Examiner* — Taylor V Oh

(57) ABSTRACT

The present invention relates to an improved crystallization procedure to obtain canagliflozin hemihydrate crystals having a narrow particle size distribution by removing a small part of the crystalline suspension in the crystallization vessel from said vessel and subjecting said part to particle size reduction of the formed crystals followed by heating and reintroducting said part of the crystalline suspension again in the crystallization vessel which is kept within a specific temperature range.

23 Claims, 3 Drawing Sheets

Figure 1 : comparison of equipment set-up of prior art process of WO-2011/003976 and the improved set-up
prior art set-up
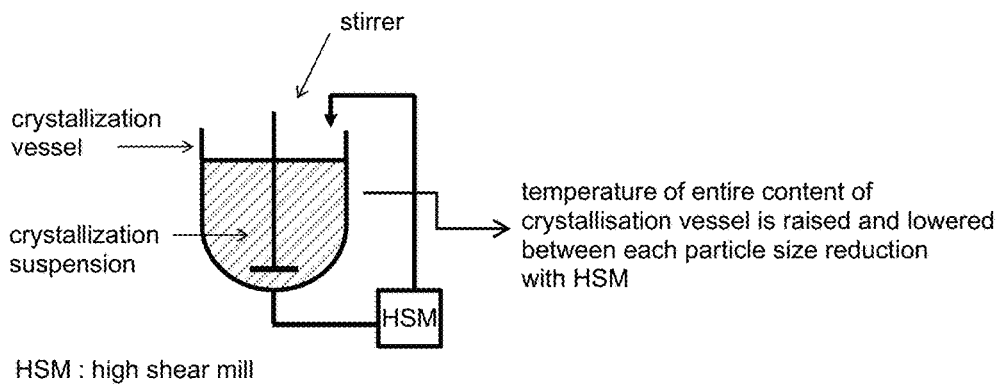
HSM : high shear mill
present invention
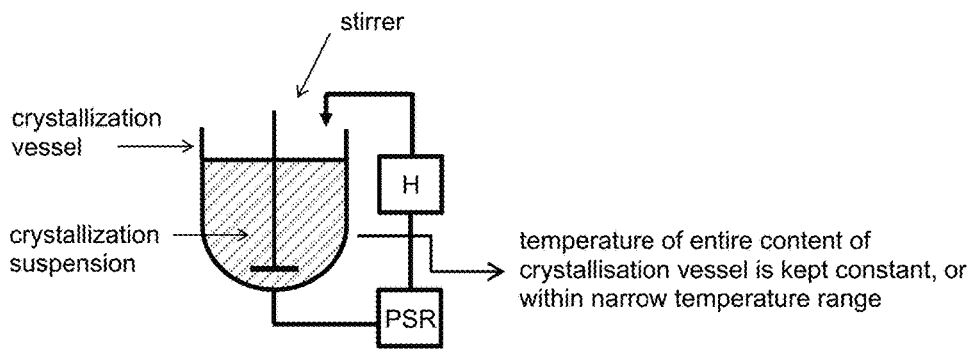
H : heating equipment
PSR : particle size reduction equipment Figure 2 : narrowing of particle size distribution by combining particle size reduction and heating
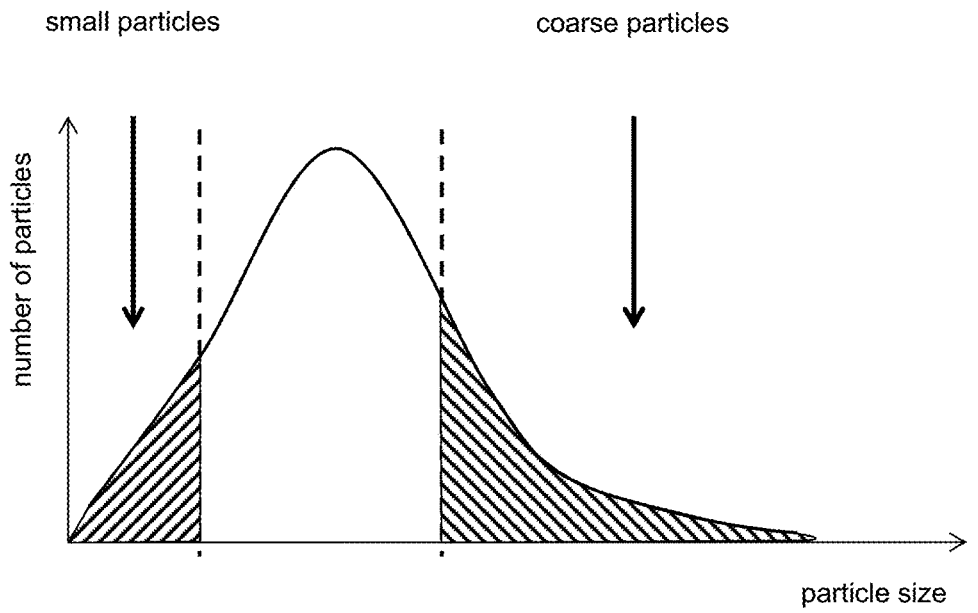
removed by heating in step e)
removed by mechanical particle size reduction in step e)
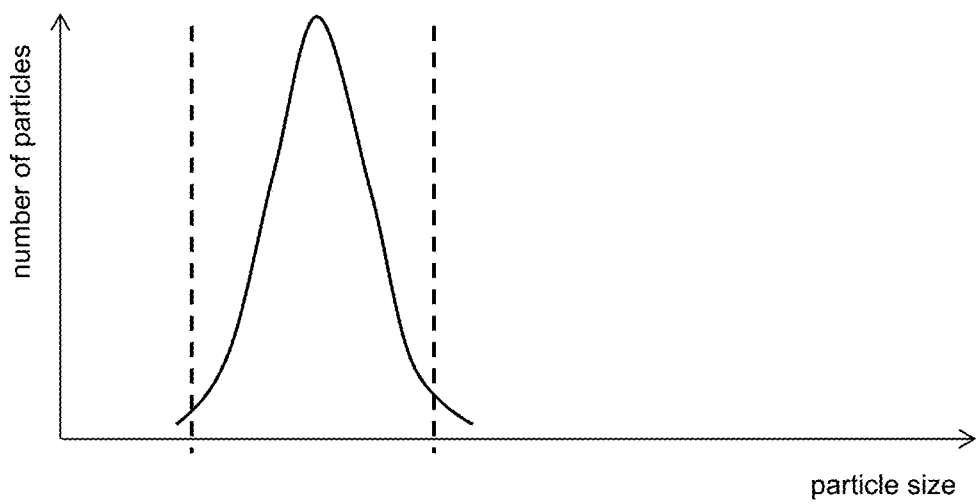

Figure 3 : particle size distribution of canagliflozin hemihydrate at the start of Example 1

Figure 4 : particle size distribution of canagliflozin hemihydrate at the end of Example 1

CRYSTALLIZATION PROCEDURE FOR OBTAINING CANAGLIFLOZIN HEMIHYDRATE CRYSTALS

CROSS REFERENCE TO RELATED APPLICATIONS

This application is a national stage of Application No. PCT/EP2016/081861, filed Dec. 20, 2016, which claims the benefit of EP application 16172070.1, filed May 31, 2016, and EP application 15201459.3, filed Dec. 21, 2015.

The present invention relates to an improved crystallization procedure to obtain canagliflozin hemihydrate crystals having a narrow particle size distribution by removing a small part of the crystalline suspension in the crystallization vessel from said vessel and subjecting said part to particle size reduction of the formed crystals followed by heating and reintroducting said part of the crystalline suspension again in the crystallization vessel which is kept within a specific temperature range.

The compound 1-(β-D-glucopyranosyl)-4-methyl-3-[5-(4-fluorophenyl)-2-thienylmethyl] benzene, known under its INN as canagliflozin, exhibits an inhibitory activity against sodium-dependent glucose transporter (SGLT), such as for example SGLT2, and is approved for use in the treatment of diabetes type II. It is described in WO-2005/012326 as compound (84) having the following structure:

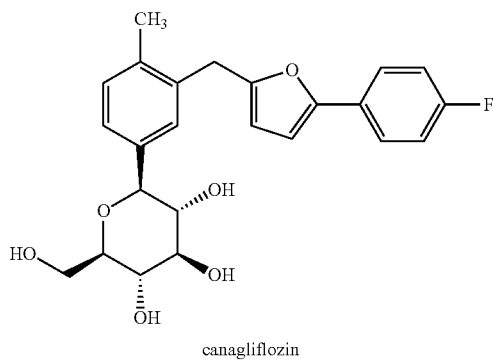 [SMILES: Cc1ccc([C@@H]2O[C@H](CO)[C@@H](O)[C@H](O)[C@H]2O)cc1Cc1ccc(-c2ccc(F)cc2)o1]

canagliflozin

A hemihydrate crystalline form of canagliflozin is disclosed in WO-2008/069327.

WO-2011/003976 discloses a crystallization procedure comprising of at least one temperature oscillation episode and at least one mechanical particle size reduction episode to obtain canagliflozin hemihydrate crystals having a narrow particle size distribution and improved flowability, bulk and tap density properties.

In general, for commercial use it is important that Active Pharmaceutical Ingredients (API's) should have good handling qualities. Additionally, there is often a need to produce the API in a pure and crystalline form to enable formulations to meet specific pharmaceutical requirements.

Crystal engineering is of importance in the production of API's. During crystallization, many physico-chemical characteristics of the API or drug substance are defined, including crystal polymorph, shape, size, particle size distribution, chemical purity and stability. These characteristics influence the stirrability, residual solvent level, drying time, agglomeration, fragmentation and attrition during the isolation process, which in turn affects the drug product manufacturing by determining particle flow, compressibility, solubility, dissolution rate and bioavailability. The specifications towards the physical properties of the API, driven by the drug product manufacturing, are very narrow concerning particle size distribution, bulk density, electrostatic charge and flowability.

WO-2011/003976 discloses a crystallization procedure that provides for canagliflozin hemihydrate crystals having a narrow particle size distribution wherein the crystallization procedure subjects the crystalline suspension in the crystallization vessel to one or more temperature oscillation episodes combined with one or more mechanical particle size reduction episodes characterized in that during each temperature or particle size reduction episode the entire content of the crystallization vessel is subjected to the temperature oscillation or particle size reduction.

The crystallization procedure of the present invention differs from the prior art procedure of WO-2011/003976 in that at any given time during the crystallization procedure only a fraction of the entire crystalline suspension in the crystallization vessel is removed from the crystallization vessel and subjected to particle size reduction of the formed crystals followed by heating and reintroducting said fraction of the crystalline suspension in the crystallization vessel which is kept at a constant temperature, or within a specific temperature range. FIG. 1 in the Drawings section provides a graphical representation of the prior art and new set-up.

This improved crystallization procedure has several advantages:
  shortening in time of the overall crystallization process;
  higher concentration of crystalline material in the crystallization vessel, which can be increased for canagliflozin hemihydrate from about 200 g/liter for the process according to WO-2011/003976 (i.e. Example 1) up to 500 g/liter;
  reduced exposure of the canaglifozin hemihydrate to increased temperatures which potentially reduces thermal breakdown: only a small amount of the entire crystallization suspension is subjected to a temperature oscillation episode, i.e. temporarily temperature increase lasting second or a few minutes, while the remaining amount of the crystallization suspension in the crystallization vessel is kept at a constant lower temperature, or within a specific—and lower—temperature range; and
  the increase in temperature during the temperature oscillation episodes can be performed with a hot heat exchanger resulting in the need for less energy since hot heat exchangers typically have a much larger surface-to-volume ratio than a traditional crystallisation vessel, resulting in a more efficient heat transfer.

When comparing the process of the present invention for the manufacture of canagliflozin hemihydrate crystals with the process claimed in WO-2011/003976, the following technical advantages occur:
  higher concentration of crystalline material in the crystallization vessel, which can be increased from 200 g/liter for the process of Example 1 in WO-2011/003976 up to about 440 to 550 g/liter as demonstrated in Examples 1 to 5 in the present invention;
  the temperature cycling/particle size reduction part of the present crystallization process is markedly shorter: in Example 1 of WO-2011/003976 the temperature cycling/particle size reduction part lasts at least 6 hours 55 minutes, while in Examples 1 to 5 of the present invention this temperature cycling/particle size reduction part lasts 2 hours.

The effect of combining particle size reduction and heating results in a narrowing of the particle size distribution as depicted in FIG. 2. Particle size reduction, e.g. by milling or sonication, results in breaking the coarse or larger crystalline particles into smaller ones, and the reheating of the resulting crystalline suspension results in a dissolution of the smaller crystalline particles. The combination of both techniques results in a narrowing of the overall particle size distribution.

A first embodiment of the present invention relates to a process for preparing canagliflozin hemihydrate crystals comprising the consecutive steps of a) preparing a solution in a crystallization vessel of canagliflozin in a solvent system comprising water in an amount from 0.37 wt % to 1.50 wt % under concentration and temperature conditions which allow the complete dissolution of canagliflozin;
b) cooling the said solution to a temperature such that crystallization will start upon addition of a seed crystal;
c) seeding the solution of step b) with crystalline canagliflozin hemihydrate;
d) cooling the solution of step c) to a temperature ranging from 35° C. to 47° C. in order to obtain a crystalline suspension;
e) removing a part of the crystalline suspension from the crystallization vessel in an amount that is less than the entire content and subjecting said part to particle size reduction, heating said part to a temperature higher than the temperature of the crystalline suspension in the crystallization vessel and returning said part back to the crystallization vessel;
f) repeating step e) until the entire content of the crystallization vessel has undergone between 0.8 and 100 turnovers;
g) isolating the crystals of crystalline canagliflozin hemihydrate thus formed.

The solvent, solvent mixture or solvent system used in the crystallization process according to the present invention can be any organic solvent, or mixture of organic solvents, that can contain water in an amount from 0.37 wt % to 1.50 wt %. For canagliflozin the solvent system is an organic alkyl ester, in particular isopropyl acetate comprising water in an amount from 0.37 wt % to 1.50 wt %.

The amount of water from 0.37 wt % to 1.50 wt % in the crystallization process of the present invention to obtain canagliflozin hemihydrate crystals can be achieved in different ways. For instance, the crystallization process can start in step a) by dissolving anhydrous canagliflozin in the solvent system and adding water till the desired amount from 0.37 wt % to 1.50 wt % is obtained. Alternatively, a hydrated form of canagliflozin, such as e.g. canagliflozin hemihydrate or canagliflozin monohydrate, can be dissolved in the solvent system and water is then added or removed, e.g. by fractional distillation, till the desired amount from 0.37 wt % to 1.50 wt % is obtained.

The temperature conditions in the crystallization process of the present invention to obtain canagliflozin hemihydrate crystals depends upon the solvent system used. For instance when the solvent system is isopropyl acetate comprising water in an amount from 0.37 wt % to 1.50 wt % the following conditions apply:

step a): the temperature ranges from 65° C. to 80° C., in particular from 70° C. to 75° C.;
step b) and step c): the temperature in the metastable zone when seed crystals are added ranges from 50° C. to 64° C., in particular from 52° C. to 60° C., more particular from 54° C. to 58° C.;
step d): in order to obtain a crystalline suspension the temperature in the crystallization vessel is a cooled to a temperature ranging from 30° C. to 49° C., or from 35° C. to 47° C., or from 38° C. to 45° C.; or from 40° C. to 42° C.; alternatively the temperature may be kept at a constant temperature not lower than 40° C., for instance 42° C.;
step e): after particle size reduction the crystalline suspension is heated to a temperature which can be the same as the temperature in the crystallization vessel or to a higher temperature but not exceeding the temperature at which the crystalline suspension was seeded in step b).

The cooling of the crystalline suspension in step b) and step d) may be done according to a specific temperature cooling profile. For instance the temperature cooling profile may be a linear profile, e.g. 0.5° C./minute, 0.75° C./minute, 1° C./minute, 2° C./minute or any other value. Alternatively, a cubic cooling profile may be used.

The heating of the crystalline suspension in step e) may be done according to a specific temperature heating profile. For instance the temperature heating profile may be a linear profile, e.g. 0.5° C./minute, 0.75° C./minute, 1° C./minute, 2° C./minute or any other value. Alternatively, a cubic heating profile may be used.

The amount of canagliflozin in step a) of the crystallization procedure can be up to 500 g/liter and in practice ranges from 200 g/liter to 500 g/liter, or from 400 g/liter to 500 g/liter.

The amount of seeding crystals used in step c) typically ranges from 0.1 w/w % to 5.0 w/w %, in particular the amount is 0.25 w/w %.

Seed crystals of crystalline canagliflozin hemihydrate for use in the crystallization procedure of the present invention can be obtained by spontaneous crystallization of canagliflozin hemihydrate from a slowly cooled supersaturated solution of canagliflozin dissolved in isopropyl acetate comprising water in an amount from 0.37 wt % to 1.50 wt % and can be used either in their isolated form or milled to finer particles. Alternatively, the seed crystals can also be prepared using the crystallisation procedures for obtaining a hemihydrate crystalline form of canagliflozin as described in WO-2008/069327 or WO-2011/003976. The seed crystals used in the working Examples 1 to 5 were prepared using the procedure of WO-2011/003976.

In step e) the amount of crystalline suspension from the crystallization vessel that is removed from the crystallization vessel and subjected to particle size reduction, heating and then returned to the crystallization vessel, is an amount that is less than the entire content of the crystallization vessel. The removed part or fraction of the entire crystalline suspension—then subjected to particle size reduction and heating—is any amount from 1% to 80%, or from 1% to 70%, or from 2% to 60% or from 5% to 50%, of the entire content of the crystallization vessel. The step of removing a part of the entire crystalline suspension and subjecting it to particle size reduction, heating and its return to the crystallization vessel is repeated in step f) until the entire content of the crystallization vessel has undergone between 0.8 and 100 turnovers.

The removal and return of a small amount of crystallization suspension from the crystallization vessel in step e) can be carried out by a pump and a conduit system. Said pump and conduit system introduces the crystallization suspension into a unit wherein the particle size reduction takes place and a unit for heating, such as one or more hot heat exchangers. When particle size reduction is performed with a shearing machine said machine can also function simultaneously as a pump system.

The isolation of the canagliflozin hemihydrate crystals in step g) from the crystallization vessel can be carried out by any conventional means, such as by filtration or centrifugation.

The particle size reduction of the canagliflozin hemihydrate crystals in suspension can be performed by wet milling or wet grinding using a shearing machine such as a high-speed rotor-stator device or high shear mill. Suitable shearing machines are e.g. of the Turrax® type, magic LAB®, or Dispax-Reactor® type, sold by IKA®-Werke GmbH & Co. KG in Germany. These high shear milling machines can use different types of milling disks such as "2G, 4M and 6F generators" depending upon the desired particle size and/or milling time.

Another method for particle size reduction can be sonication whereby the crystalline suspension is subjected to sonication energy whose frequency is above that which is detectable by the human ear: i.e. higher than 16 kHz to 20 kHz using an ultrasound probe inserted in the crystalline suspension.

Particle size analysis of canagliflozin hemihydrate crystals in suspension during the crystallization process can be performed with light scattering techniques such as focused beam reflectance measurement (FBRM) using e.g. the Lasentec® products from Mettler-Toledo. Alternatively, samples can be taken at different times during the crystallisation procedure and analysed using laser diffraction techniques with suitable equipment such as e.g. a Malvern Mastersizer 2000 laser diffractometer (Malvern, UK).

After particle size reduction, and before the crystalline suspension is returned to the crystallization vessel, said suspension is heated to a temperature equal to or slightly higher than the temperature of the crystalline suspension in the crystallization vessel. During heating the smallest crystalline particles dissolve and can recrystallize in the crystallization vessel. The combination of the particle size reduction—which results in breaking the larger crystalline particles into smaller ones—and the reheating—which results in dissolution of the smaller crystalline particles—results in a narrowing of the overall particle size distribution.

Reheating the crystalline suspension after particle size reduction can be done with one or more hot heat exchangers or any other means known by the skilled person such as e.g. a small crystallization vessel.

The sequence of feeding part of the crystalline suspension in the crystallization vessel to the externally placed shearing machine, reheating with one or more hot heat exchangers, and return to the crystallization vessel is repeated until the desired particle size distribution is obtained. In general, the more the number of turnovers, the narrower the particle size distribution becomes. One turnover of the crystalline suspension in the crystallization vessel corresponds to the complete volume of the crystallization suspension that has undergone the particle size reduction step and concomitant reheating step. In practice, the number of such turnovers ranges from 0.8 to 100, or from 5 to 50, or 10 to 40.

In a further embodiment the crystallization process for preparing canagliflozin hemihydrate crystals as explained above can also be used for crystallizing any other drug substance. Hence the present invention also relates to a process for preparing a crystalline drug substance comprising the consecutive steps of
a) preparing a solution or suspension in a crystallization vessel of said drug substance in a solvent;
b) cooling the said solution to a temperature such that the solution is in the metastable zone wherein nucleation is possible;
c) optionally seeding the solution of step b) with drug substance crystals;
d) cooling the solution of step c) to obtain a suspension of crystalline drug substance;
e) removing a part of the crystalline suspension from the crystallization vessel in an amount that is less than the entire content and subjecting said part to particle size reduction, heating said part to a temperature higher than the temperature of the crystalline suspension in the crystallization vessel and returning said part back to the crystallization vessel;
f) repeating step e) until the entire content of the crystallization vessel has undergone a sufficient number of turnovers until a desired particle size distribution is obtained;
g) optionally lowering the temperature of the crystalline suspension in the crystallization vessel and isolating the crystalline drug substance thus formed.

The metastable zone in step b) is an area in the concentration/temperature solubility diagram wherein spontaneous nucleation to form crystals does not occur immediately and either further cooling is needed or the addition of a seed crystal is needed to start crystallization.

The solvent used in the crystallisation process for preparing crystalline drug substances according to the present invention can be any solvent, or mixture of solvents, wherein the solubility of the drug substance is dependent upon the temperature. Suitable solvents are e.g. water or an organic solvent such as e.g. methanol, ethanol, propanol, isopropanol, ethyl acetate, isopropyl acetate, acetone, 2-butanone, dichloromethane, diethyl ether, methyl tert-butyl ether, dioxane, toluene, pentane, hexane, cyclohexane, petroleum ether, and the like, or any mixture thereof.

In step c) the use of seeding crystals to obtain crystalline drug substance is not always required and is therefore an optional step. If seeding crystals are used the amount typically ranges from 0.1 w/w % to 5.0 w/w %.

The removal and return of a small amount of crystallization suspension from the crystallization vessel in step e) can be carried out by a pump and a conduit system. Said pump and conduit system introduces the crystallization suspension into a unit wherein the particle size reduction of the crystalline drug substance takes place and a unit for heating, such as one or more hot heat exchangers. When particle size reduction is performed with a shearing machine said machine can also function simultaneously as a pump system.

The particle size reduction of the crystalline drug substance in suspension can be performed by wet milling or wet grinding using a shearing machine such as a high-speed rotor-stator device or high shear mill. Suitable shearing machines are e.g. of the Turrax® type, magic LAB®, or Dispax-Reactor® type, sold by IKA®-Werke GmbH & Co. KG in Germany. These high shear milling machines can use different types of milling disks such as "2G, 4M and 6F generators" depending upon the desired particle size and/or milling time.

Another method for particle size reduction can be sonication whereby the crystalline suspension of crystalline drug substance is subjected to sonication energy whose frequency is above that which is detectable by the human ear: i.e. higher than 16 kHz to 20 kHz using an ultrasound probe inserted in the crystalline suspension.

The isolation of the crystalline drug substance in step g) from the crystallization vessel can be carried out by any conventional means, such as by filtration or centrifugation.

The term 'drug substance' as used in this text is an 'active ingredient' which is any component of a drug product intended to furnish pharmacological activity or other direct effect in the diagnosis, cure, mitigation, treatment, or prevention of disease, or to affect the structure or any function of the body of humans or other animals. Active ingredients include those components of the product that may undergo chemical change during the manufacture of the drug product and be present in the drug product in a modified form intended to furnish the specified activity or effect.

EXAMPLE 1

A solution of canagliflozin (1 mol) in isopropyl acetate (1.0 liter) was heated till 70° C. and filtered over a charcoal filter. The solution was introduced in the crystallization vessel and the amount of water was adjusted to 1.05 wt %.

The solution in the crystallization vessel was stirred, cooled to 54° C., seeded with canagliflozin hemihydrate crystals (1.13 g, 0.25 w/w %) and stirred for 15 minutes. The crystallization suspension in the crystallization vessel was cooled to 42° C. using a linear cooling profile and kept at 40° C.

Then an amount of the crystallization suspension was pumped (1600 mL/min) through a high shear mill (Dispax-Reactor® type DR 2000/20 from IKA®-Werke GmbH & Co. KG in Germany with a 2P milling disk), heated with a hot heat exchanger to a temperature of 55° C. and returned to the crystallization vessel. The high shear milling, heating, and pumping back into the crystallization vessel was performed for 2 hours and then stopped.

The crystallisation suspension was stirred for 15 minutes and then cooled to 20° C. while simultaneously dosing isopropylacetate (1.116 liter) the canagliflozin hemihydrate crystals were isolated by filtration, washed with isopropyl acetate and dried under vacuum.

For canaglifozin hemihydrate the graphical representation of the particle size distribution obtained by a classical cooling crystallisation process can be found in FIG. 3. The particle size distribution of canaglifozin hemihydrate obtained after performing the crystallization procedure of Example 1 is represented in FIG. 4. As can be seen by comparing both particle size distribution figures, the particle size distribution of crystalline canaglifozin hemihydrate obtained using process of the present invention does not show the presence of a double distribution and has a narrower particle size distribution.

EXAMPLE 2

A solution of canagliflozin (1 mol) in isopropyl acetate (1.0 liter) was heated till 72° C. and filtered over a charcoal filter. The solution was introduced in the crystallization vessel and the amount of water was adjusted to 1.05 wt %.

The solution in the crystallization vessel was stirred, cooled to 56° C., seeded with canagliflozin hemihydrate crystals (1.13 g, 0.25 w/w %) and stirred for 15 minutes.

The crystallization suspension in the crystallization vessel was cooled to 42° C. using a linear cooling profile and kept at 42° C.

Then an amount of the crystallization suspension was pumped (1600 mL/min) through a high shear mill (Dispax-Reactor® type DR 2000/20 from IKA®-Werke GmbH & Co. KG in Germany with a 2P or 4M milling disk), heated with a hot heat exchanger to a temperature of 53° C. and returned to the crystallization vessel. The high shear milling, heating, and pumping back into the crystallization vessel was performed for 2 hours and then stopped.

The crystallisation suspension was stirred for 15 minutes and then cooled to 18° C. while simultaneously dosing isopropylacetate (1.116 liter) the canagliflozin hemihydrate crystals were isolated by filtration, washed with isopropyl acetate and dried under vacuum.

EXAMPLE 3

A solution of canagliflozin (1.25 mol) in isopropyl acetate (1.0 liter) was heated till 72° C. and filtered over a charcoal filter. The solution was introduced in the crystallization vessel and the amount of water was adjusted to 1.10 wt %.

The solution in the crystallization vessel was stirred, cooled to 56° C., seeded with canagliflozin hemihydrate crystals (1.27 g, 0.25 w/w %) and stirred for 15 minutes.

The crystallization suspension in the crystallization vessel was cooled to 42° C. using a linear cooling profile and kept at 42° C.

Then an amount of the crystallization suspension was pumped (1600 mL/min) through a high shear mill (Dispax-Reactor® type DR 2000/20 from IKA®-Werke GmbH & Co. KG in Germany with a 2P and 4M milling disk), heated with a hot heat exchanger to a temperature of 55° C. and returned to the crystallization vessel. The high shear milling, heating, and pumping back into the crystallization vessel was performed for 2 hours and then stopped.

The crystallisation suspension was stirred for 15 minutes and then cooled to 18° C. while simultaneously dosing isopropylacetate (1.116 liter) the canagliflozin hemihydrate crystals were isolated by filtration, washed with isopropyl acetate and dried under vacuum.

EXAMPLE 4

A solution of canagliflozin (1 mol) in isopropyl acetate (1.0 liter) was heated till 70° C. and filtered over a charcoal filter. The solution was introduced in the crystallization vessel and the amount of water was adjusted to 1.10 wt %.

The solution in the crystallization vessel was stirred, cooled to 56° C., seeded with canagliflozin hemihydrate crystals (1.13 g, 0.25 w/w %) and stirred for 15 minutes.

The crystallization suspension in the crystallization vessel was cooled to 42° C. using a linear cooling profile and kept at 42° C.

Then an amount of the crystallization suspension was pumped (1600 mL/min) through a high shear mill (Dispax-Reactor® type DR 2000/20 from IKA®-Werke GmbH & Co. KG in Germany with 2P, 4M and 6F milling disks), heated with a hot heat exchanger to a temperature of 55° C. and returned to the crystallization vessel. The high shear milling, heating, and pumping back into the crystallization vessel was performed for 2 hours and then stopped.

The crystallisation suspension was stirred for 15 minutes and then cooled to 18° C. while simultaneously dosing isopropylacetate (1.116 liter) the canagliflozin hemihydrate crystals were isolated by filtration, washed with isopropyl acetate and dried under vacuum.

EXAMPLE 5

A solution of canagliflozin (1 mol) in isopropyl acetate (1.0 liter) was heated till 70° C. and filtered over a charcoal filter. The solution was introduced in the crystallization vessel and the amount of water was adjusted to 1.15 wt %.

The solution in the crystallization vessel was stirred, cooled to 58° C., seeded with canagliflozin hemihydrate crystals (1.13 g, 0.25 w/w %) and stirred for 15 minutes. The crystallization suspension in the crystallization vessel was cooled to 42° C. using a linear cooling profile and kept at 42° C.

Then an amount of the crystallization suspension was pumped (1600 mL/min) through a high shear mill (Dispax-Reactor® type DR 2000/20 from IKA®-Werke GmbH & Co. KG in Germany with a 2P milling disk), heated with a hot heat exchanger to a temperature of 57° C. and returned to the crystallization vessel. The high shear milling, heating, and pumping back into the crystallization vessel was performed for 2 hours and then stopped.

The crystallisation suspension was stirred for 15 minutes and then cooled to 18° C. while simultaneously dosing isopropylacetate (1.116 liter) the canagliflozin hemihydrate crystals were isolated by filtration, washed with isopropyl acetate and dried under vacuum.

EXAMPLE 6

A suspension of the MTP inhibitor (+)-phenyl-(4-{4-[(4'-trifluoromethyl-biphenyl-2-carbonyl)-amino]-phenyl}-piperidin-1-yl)-acetic acid methyl ester (204 g, 0.357 mol) in isopropanol (1781 mL) was heated till 75° C. The solution in the crystallization vessel was stirred, cooled to 67° C., seeded with MTP crystals (1.5 g, 0.5 w/w %) and stirred for 2 hours. The crystallization suspension in the crystallization vessel was cooled to 58° C. using a nonlinear cooling profile of 1.5 hours. Then an amount of the crystallization suspension was pumped (1600 mL/min) through a high shear mill (Dispax-Reactor® type DR 2000/20 from IKA®-Werke GmbH & Co. KG in Germany with a 2P and 4M milling disk), heated with a hot heat exchanger to a temperature of 63° C. and returned to the crystallization vessel. The high shear milling, heating (successively 63° C., 60° C. and 57° C.), and pumping back into the crystallization vessel was performed for 3 hours 20 minutes while cooling nonlinearly to 20° C.

EXAMPLE 7

A suspension of the MTP inhibitor (+)-phenyl-(4-{4-[(4'-trifluoromethyl-biphenyl-2-carbonyl)-amino]-phenyl}-piperidin-1-yl)-acetic acid methyl ester (204 g, 0.357 mol) in isopropanol (1781 mL) was heated till 75° C. The solution in the crystallization vessel was stirred, cooled until spontaneous crystallization occurs. Heat up until stirrable (68° C.). The crystallization suspension in the crystallization vessel was cooled to 58° C. using a nonlinear cooling profile of 1.5 hours. Then an amount of the crystallization suspension was pumped (1600 mL/min) through a high shear mill (Dispax-Reactor® type DR 2000/20 from IKA®-Werke GmbH & Co. KG in Germany with a 2P and 4M milling disk), heated with a hot heat exchanger to a temperature of 63° C. and returned to the crystallization vessel. The high shear milling, heating (successively 63° C., 60° C. and 57° C.), and pumping back into the crystallization vessel was performed for 3 hours 20 minutes while cooling nonlinearly to 20° C.

DESCRIPTION OF THE DRAWINGS

FIG. 1: comparison of equipment set-up of prior art process of WO-2011/003976 and the improves set-up using an externally placed shearing machine and a hot heat exchanger FIG. 2: narrowing of particle size distribution by combining particle size reduction and heating FIG. 3: particle size distribution of canagliflozin hemihydrate at the start of Example 1

FIG. 4: particle size distribution of canagliflozin hemihydrate at the end of Example 1

The invention claimed is:

1. A process for preparing canagliflozin hemihydrate crystals comprising the consecutive steps of
    a) preparing a solution in a crystallization vessel of canagliflozin in a solvent system comprising water in an amount from 0.37 wt % to 1.50 wt % under concentration and temperature conditions which allow the complete dissolution of canagliflozin;
    b) cooling the said solution to a temperature such that crystallization will start upon addition of a seed crystal;
    c) seeding the solution of step b) with crystalline canagliflozin hemihydrate;
    d) cooling the solution of step c) to a temperature ranging from 35° C. to 47° C. in order to obtain a crystalline suspension;
    e) removing a part of the crystalline suspension from the crystallization vessel in an amount that is less than the entire content and subjecting said part to particle size reduction, heating said part to a temperature higher than the temperature of the crystalline suspension in the crystallization vessel and returning said part back to the crystallization vessel;
    f) repeating step e) until the entire content of the crystallization vessel has undergone between 0.8 and 100 turnovers;
    g) isolating the crystals of crystalline canagliflozin hemihydrate thus formed.

2. The process as claimed in claim 1 wherein the solvent system is an organic alkyl ester.

3. The process as claimed in claim 1 wherein canagliflozin in step a) is added to the solvent system in the form of anhydrous canagliflozin.

4. The process as claimed in claim 1 wherein canagliflozin in step a) is added to the solvent system in the form of a hemihydrate or a monohydrate.

5. The process as claimed in claim 3 wherein the temperature in step a) is from 65° C. to 80° C.

6. The process as claimed in claim 5 wherein the temperature in step b) ranges from 50° C. to 64° C.

7. The process as claimed in claim 1 wherein the temperature in step d) ranges from 30° C. to 49° C.

8. The process as claimed in claim 1 wherein the amount of canagliflozin in step a) ranges from 200 g/liter to 500 g/liter.

9. The process as claimed in claim 1 wherein the amount of seeding crystals used in step c) ranges from 0.1 wt % to 1.0 wt %.

10. The process as claimed in claim 1 wherein in step e) the removed part of crystalline suspension that is subjected to particle size reduction, heating and return to the crystallization vessel is in an amount that ranges from 1% to 80%, of the entire content of the crystallization vessel.

11. The process as claimed in claim 9 wherein the number of turnovers in step f) is from 5 to 50.

12. The process as claimed in claim 2 wherein the organic alkyl ester is isopropyl acetate.

13. The process as claimed in claim 5 wherein the temperature in step a) is from 70° C. to 75° C.

14. The process as claimed in claim 6 wherein the temperature in step b) ranges from 52° C. to 60° C.

15. The process as claimed in claim 14 wherein the temperature in step b) ranges from 54° C. to 58° C.

16. The process as claimed in claim 7 wherein the temperature in step d) ranges from 35° C. to 47° C.

17. The process as claimed in claim 16 wherein the temperature in step d) ranges from 38° C. to 45° C.

18. The process as claimed in claim 17 wherein the temperature in step d) ranges from 40° C. to 42° C.

19. The process as claimed in claim 8 wherein the amount of canagliflozin in step a) ranges from 400 g/liter to 500 g/liter.

20. The process as claimed claim 10 wherein in step e) the removed part of crystalline suspension that is subjected to particle size reduction, heating and return to the crystallization vessel is in an amount that ranges from 1% to 70% of the entire content of the crystallization vessel.

21. The process as claimed claim 20 wherein in step e) the removed part of crystalline suspension that is subjected to particle size reduction, heating and return to the crystallization vessel is in an amount that ranges from 2% to 60% of the entire content of the crystallization vessel.

22. The process as claimed claim 21 wherein in step e) the removed part of crystalline suspension that is subjected to particle size reduction, heating and return to the crystallization vessel is in an amount that ranges from 5% to 50% of the entire content of the crystallization vessel.

23. The process as claimed in claim 11 wherein the number of turnovers in step f) is from 10 to 40.

* * * * *